(12) United States Patent (10) Patent No.: US 12,161,582 B2
Cao (45) Date of Patent: Dec. 10, 2024

(54) PHYSIOTHERAPY INSTRUMENT WITH INTELLIGENT HEATING CONTROL FUNCTION BASED ON BIOELECTRIC FEEDBACK

(71) Applicant: FAMIDOC TECHNOLOGY CO., LTD., Dongguan (CN)

(72) Inventor: Liang Cao, Shenzhen (CN)

(73) Assignee: FAMIDOC TECHNOLOGY CO., LTD., Dongguan (CN)

( * ) Notice: Subject to any disclaimer, the term of this patent is extended or adjusted under 35 U.S.C. 154(b) by 462 days.

(21) Appl. No.: 17/456,647

(22) Filed: Nov. 29, 2021

(65) Prior Publication Data

US 2022/0079806 A1 Mar. 17, 2022

(30) Foreign Application Priority Data

Oct. 7, 2021 (CN) .......................... 202111167431.3

(51) Int. Cl.
*A61F 7/00* (2006.01)
(52) U.S. Cl.
CPC ...... *A61F 7/007* (2013.01); *A61F 2007/0071* (2013.01)

(58) Field of Classification Search
CPC ............. A61F 7/007; A61F 2007/0071; A61F 2007/0088; A61F 2007/0093
See application file for complete search history.

(56) References Cited

U.S. PATENT DOCUMENTS

| 9,710,607 B2* | 7/2017 | Ramdas ................. G16H 20/10 |
| 2014/0024882 A1* | 1/2014 | Chornenky ............... A61F 7/02 |
| | | 600/14 |
| 2014/0194797 A1 | 7/2014 | Chen |
| 2014/0309480 A1 | 10/2014 | Wang |
| 2015/0202434 A1 | 7/2015 | Liu |

* cited by examiner

*Primary Examiner* — Kaitlyn E Smith
*Assistant Examiner* — Bradford C. Blaise
(74) *Attorney, Agent, or Firm* — Hemisphere Law, PLLC; Zhigang Ma

(57) ABSTRACT

A physiotherapy instrument with an intelligent heating control function based on bioelectric feedback comprises an MCU, a boost control circuit, a pulse output control circuit, a bioelectric feedback circuit and a heating control circuit. The MCU is connected to the boost control circuit, the pulse output control circuit, the bioelectric feedback circuit and the heating control circuit. The pulse output control circuit inputs electric pulses within a safe range to a human body by means of an electrode. The bioelectric feedback circuit feeds one or multiple electric parameters, including a resistance, voltage, current and frequency of the human body, back to the MCU.

5 Claims, 4 Drawing Sheets

PHYSIOTHERAPY INSTRUMENT WITH INTELLIGENT HEATING CONTROL FUNCTION BASED ON BIOELECTRIC FEEDBACK

BACKGROUND OF THE INVENTION

1. Technical Field

The invention relates to the technical field of physiotherapy equipment, in particular to a physiotherapy instrument with an intelligent heating control function based on bioelectric feedback.

2. Description of Related Art

Electric pulse physiotherapy instruments transmit electric pulse signals with a certain voltage and frequency to human bodies by means of electrodes. Because of the electric characteristics of many constituent parts of human tissues, the muscles, nerves, body fluid and blood of human bodies will produce physicochemical reactions to some extent when the bodies receive electric stimuli. Low-frequency electrotherapy instruments and medium-frequency electrotherapy instruments are the most common electric pulse physiotherapy instruments. Electrotherapy is used in hospitals to fulfill certain therapeutic effects in relieving pains and regulating the neurological function.

However, to improve the comfort of use and physiotherapeutic effect for users, physiotherapy instruments with some functions on the present market have different heating intensities, which are controlled by users by adjusting the heating gear. Clearly, such a control method puts forward extremely high requirements for physiotherapy techniques and cannot be easily mastered by common people or the elderly.

BRIEF SUMMARY OF THE INVENTION

To overcome the above-mentioned defects of the prior art, the objective of the invention is to provide a physiotherapy instrument with an intelligent heating control function based on bioelectric feedback.

To fulfill the above objective, the invention adopts the following technical solution:

A physiotherapy instrument with an intelligent heating control function based on bioelectric feedback comprises an MCU, a boost control circuit, a pulse output control circuit, a bioelectric feedback circuit and a heating control circuit, wherein the MCU is connected to the boost control circuit, the pulse output control circuit, the bioelectric feedback circuit and the heating control circuit, the pulse output control circuit inputs electric pulses within a safe range to a human body by means of an electrode, the bioelectric feedback circuit feeds one or multiple electric parameters, including a resistance, voltage, current and frequency of the human body, back to the MCU, and the MCU controls a heating time of a heating element by means of the heating control circuit according to different parameters fed back by the bioelectric feedback circuit, so as to control a temperature to rise or fall.

Preferably, the boost control circuit comprises an inductor, a first triode and a second triode, wherein a base of the first triode is connected to a PUMP pin of the MCU by means of a first resistor, the inductor has a terminal to which a power source is accessed, as well as a terminal connected to a collector of the first triode, the collector of the first triode is connected with a diode and is connected to a positive pole of the diode, a negative pole of the diode is connected to the pulse output control circuit, is grounded by means of a charging capacitor and is connected to a collector of the second triode by means of a third resistor, and a base of the second triode is connected to a DIS_P pin of the MCU by means of a second resistor.

Preferably, the pulse output control circuit comprises a fourth triode, a fifth triode, a sixth triode and a seventh triode, wherein a base of the fourth triode, a base of the fifth triode, a base of the sixth triode and a base of the seventh triode are connected to an M_2 pin, an M_0 pin, an M_3 pin and an M_1 pin of the MCU by means of a sixth resistor, a fifth resistor, an eighth resistor and a seventh resistor respectively, an emitter of the fifth triode and an emitter of the seventh triode are connected to an output terminal of the boost control circuit, a collector of the fifth triode and an emitter of the fourth triode are connected and are both connected to the electrode, a collector of the seventh triode and an emitter of the sixth triode are connected and are both connected to the other terminal of the electrode, and a collector of the fourth triode and a collector of the sixth triode are both connected to the bioelectric feedback circuit.

Preferably, the bioelectric feedback circuit comprises an eleventh resistor and a fourth resistor, wherein the eleventh resistor has a terminal grounded and a terminal connected to the fourth resistor and the pulse output control circuit, and the other terminal of the fourth resistor is grounded by means of a first capacitor and is connected to a B_DET pin of the MCU.

Preferably, the heating control circuit comprises a third triode and an eighth triode, wherein a base of the third triode is grounded by means of a tenth resistor and is connected to a HEAT pin of the MCU by means of a ninth resistor, a collector of the third triode is connected to a base of the eighth triode, a power source is accessed to an emitter of the eighth triode, a collector of the eight triode is connected to the heating element, and the other end of the heating element is grounded by means of a resettable fuse.

By adoption of the above solution, pulses are input to a human body, and the condition of the human body is determined according to one or multiple electric parameters including the resistance, current, voltage and frequency during pulse physiotherapy to regulate the temperature properly to carry out a corresponding thermal therapy, so that intelligent treatment based on automatic temperature regulation is realized according to different physiological conditions of the human body.

DETAILED DESCRIPTION OF THE INVENTION

Figure 1:
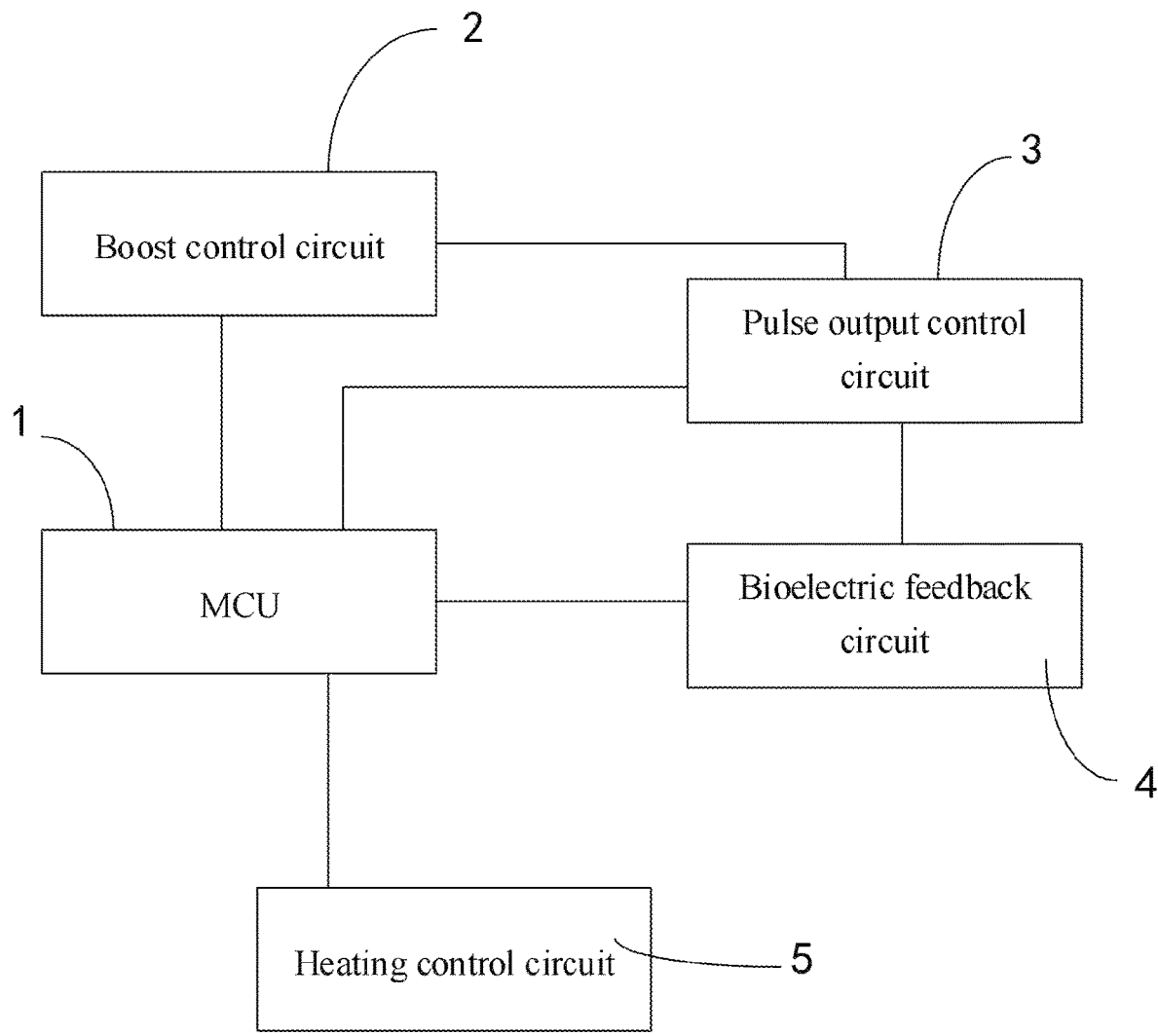
FIG. 1 is a structure and principle diagram of one embodiment of the invention.
Figure 2:
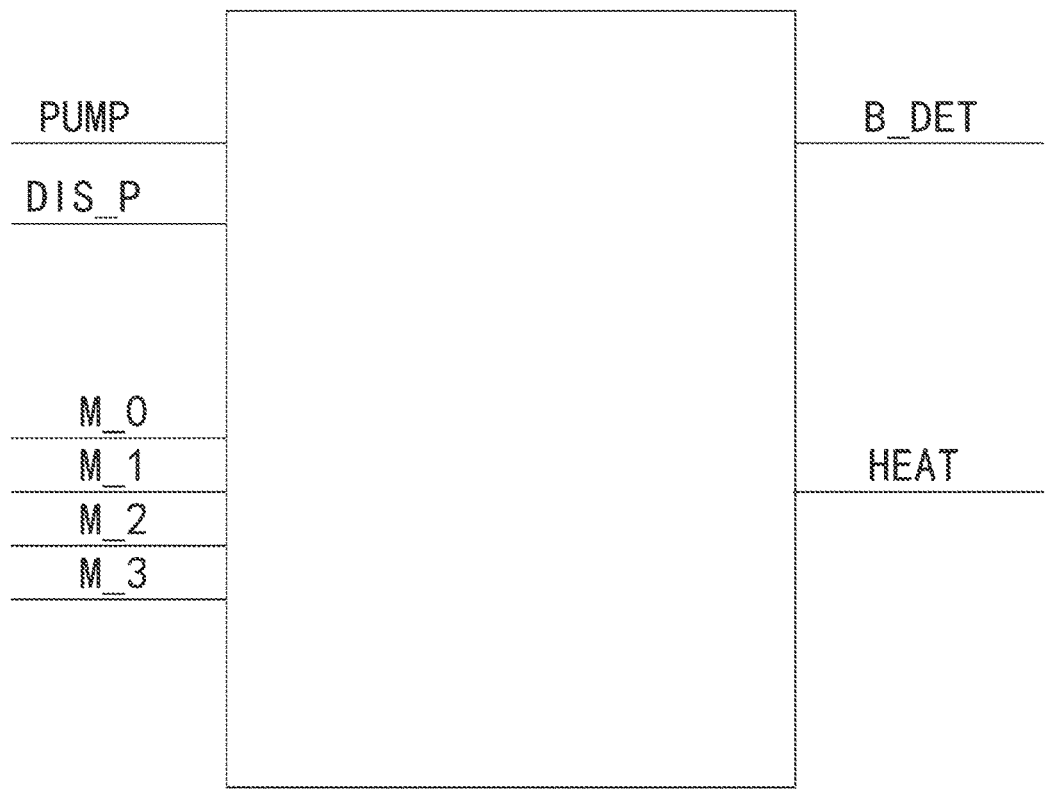
FIG. 2 is a structural diagram of an MCU according to one embodiment of the invention.

The embodiments of the invention will be described in detail below in conjunction with the accompanying drawings. Clearly, the invention may be implemented in different manners defined and covered by the claims.

As shown in FIG. 1 to FIG. 6, this embodiment provides a physiotherapy instrument with an intelligent heating control function based on bioelectric feedback, comprising an MCU 1, a boost control circuit 2, a pulse output control circuit 3, a bioelectric feedback circuit 4, and a heating control circuit 5, wherein the MCU 1 is connected to the boost control circuit 2, the pulse output control circuit 3, the bioelectric feedback circuit 4 and the heating control circuit 5, the pulse output control circuit 3 inputs electric pulses within a safe range to a human body by means of an electrode, the bioelectric feedback circuit 4 feeds one or more electric parameters, including the resistance, voltage, current and frequency of the human body, back to the MCU 1, and the MCU 1 controls the heating time of a heating element by means of the heating control circuit 5 according to different resistances fed back by the bioelectric feedback circuit 4, so as to control the temperature to rise or fall.

In this embodiment, the MCU 1 may be an XWIC035 MCU, a PUMP pin of the MCU 1 outputs a PWM signal to the boost control circuit 2, the PUMP pin and a DIS_P pin of the MCU 1 are GPIO output ports and are used for discharge control of the boost control circuit 2, M_0, M_1, M_2 and M_3 pins of the MCU 1 are GPIO output ports and are used for controlling pulses output to the human body, a HEAT pin of the MCU 1 is a GPIO port and is used for on-off control of a product heating module, and a B_DET pin of the MCU 1 is an AD detection port and is used for collecting a current fed back by the human body during work. The MCU 1 controls a voltage rise and a pulse output according to a therapy program selected by users, collects the current, fed back by the human body, on the B_DET pin by means of the AD port, and obtains, by calculation, a corresponding resistance of the target human body, so as to determine the physiological condition of the human body. Humans in different physiological conditions are classified into such as: sensitive, common and insensitive. Then, the heating temperature range is controlled according to different user groups. Refer to the following table:

| Resistance fed back | Corresponding user group | Controlled temperature |
|---|---|---|
| Less than 500Ω | Sensitive | 36-38° C. |
| 500~10KΩ | Common | 38-40° C. |
| Over 10KΩ | Insensitive | 40-42° C. |

According to this table, the MCU 1 controls the PWM duty ratio of the heating control circuit 5 to realize automatic temperature regulation. It should be noted that the relationship between the resistance fed back and the controlled temperature in the above table is merely an example, and category differences of the collected electric parameters and variations of relating values still fall within the protection scope of this embodiment.

Figure 3:
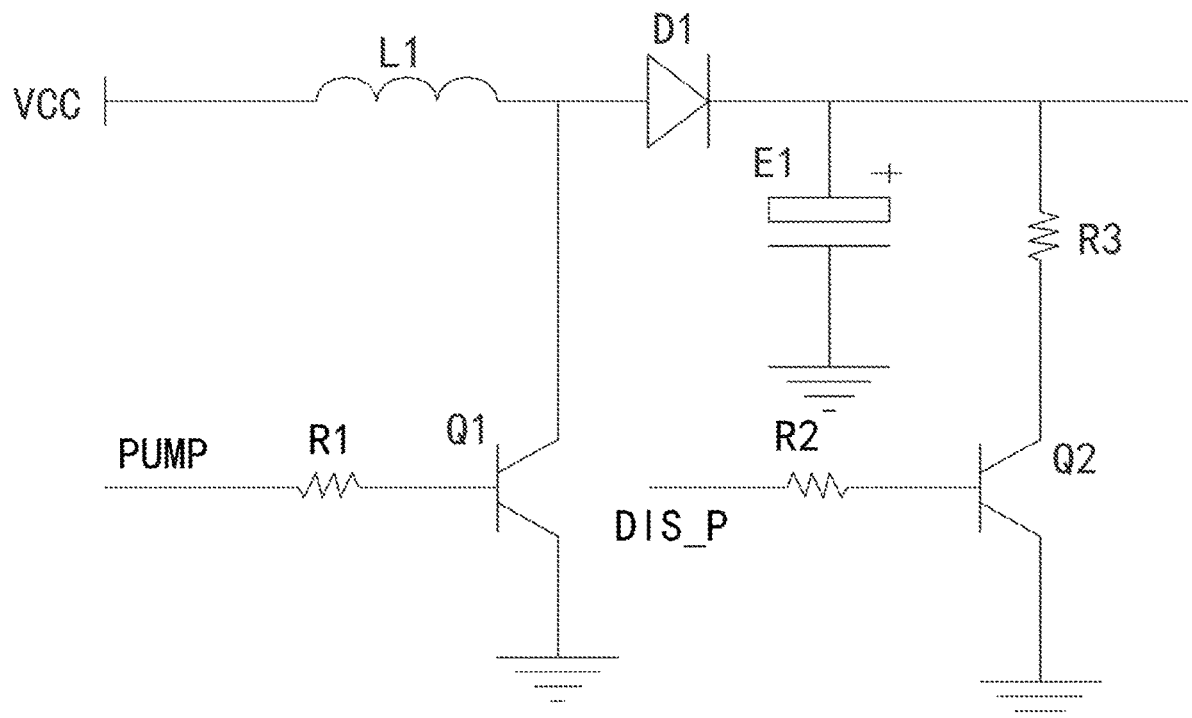
FIG. 3 is a structural diagram of a boost control circuit according to one embodiment of the invention.

Further, the boost control circuit 2 in this embodiment may adopt a circuit structure shown in FIG. 3. That is, the boost control circuit 2 comprises an inductor L1, a first triode Q1 and a second triode Q2, wherein a base of the first triode Q1 is connected to the PUMP pin of the MCU 1 by means of a first resistor R1, a power source is accessed to one terminal of the inductor L1, the other terminal of the inductor L1 is connected to a collector of the first triode Q1, the collector of the first triode Q1 is connected with a diode D1 and is connected to a positive pole of the diode D1, a negative pole of the diode D1 is connected to the pulse output control circuit 4, the negative pole of the diode D1 is grounded by means of a charging capacitor E1 and is connected to a collector of the second triode Q2 by means of a third resistor R3, and a base of the second triode Q2 is connected to the DIS_P pin of the MCU 1 by means of a second resistor R2. A boost part of the circuit is based on the bootstrap principle; when an output of the PUMP pin of the MCU 1 is high, the first triode Q1 is turned on, the power source VCC discharges to the ground by means of the inductor L1, the diode D1 prevents the voltage in the charging capacitor E1 from flowing back, and because the current in the DC inductor increases linearly in a certain proportion, energy is stored in the inductor L1 with the increase of the current; and when the output of the PUMP pin of the MCU 1 is low, the first triode Q1 is turned off, and because of the current holding characteristic of the inductor L1, the current across the inductor L1 will slowly turn into 0 at the end of charging rather than immediately turning into 0. Since the original circuit has been disconnected, the inductor L1 has to discharge by means of a new circuit, that is, the inductor L1 starts to charge the capacitor E1, and the voltage across the two terminals of the capacitor E1 rises to exceed an input voltage, so that boosting is completed. The DIS_P pin of the MCU 1 outputs a low level at ordinary times, and the second triode Q2 is turned off; and when boosting is not needed or the boost level needs to be decreased, the DIS_P pin of the MCU 1 outputs a high level, the second triode Q2 is turned on, and the terminal voltage of the capacitor E1 discharges by means of the second triode Q2.

Figure 4:
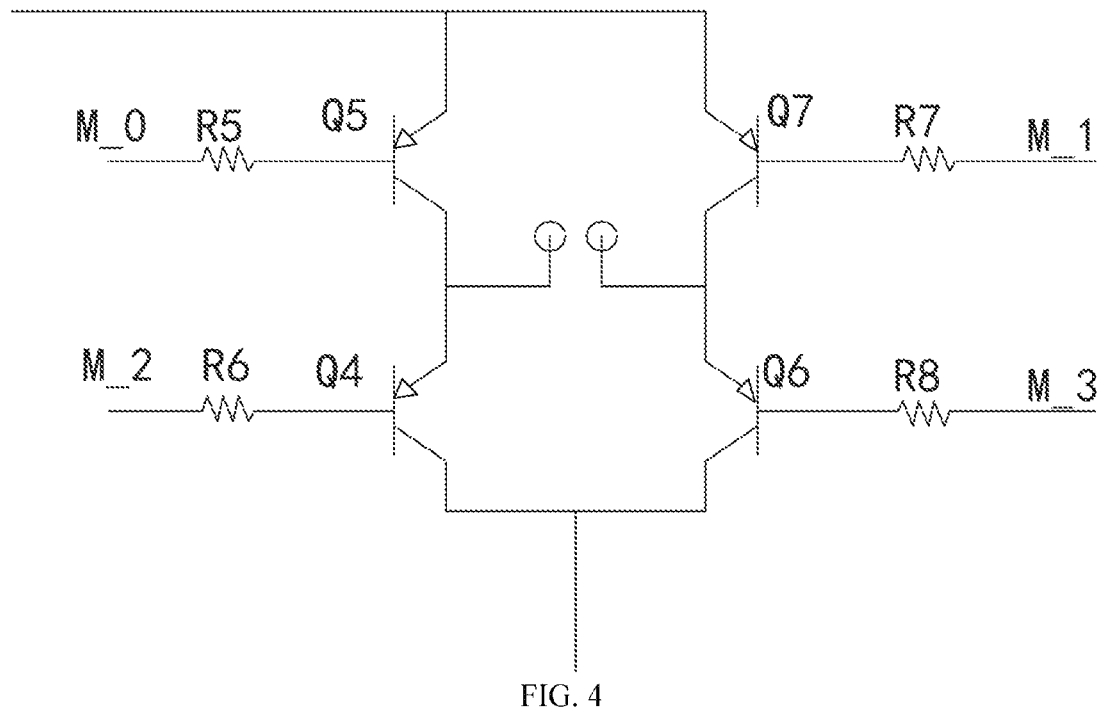
FIG. 4 is a structural diagram of a pulse output control circuit according to one embodiment of the invention.

Further, the pulse output control circuit 3 in this embodiment may adopt a circuit structure shown in FIG. 4. That is, the pulse output control circuit 3 comprises a fourth triode Q4, a fifth triode Q5, a sixth triode Q6 and a seventh triode Q7, wherein a base of the fourth triode Q4, a base of the fifth triode A5, a base of the sixth triode A6 and a base of the seventh triode Q7 are connected to the M_2 pin, the M_0 pin, the M_3 pin and the M_1 pin of the MCU 1 by means of a sixth resistor R6, a fifth resistor R5, an eighth resistor R8 and a seventh resistor R7 respectively, an emitter of the fifth triode Q5 and an emitter of the seventh triode Q7 are connected to an output terminal of the boost control circuit 2, a collector of the fifth triode Q5 and an emitter of the fourth triode Q4 are connected and are both connected to the electrode, a collector of the seventh triode Q7 and an emitter of the sixth triode Q6 are connected and are both connected to the other terminal of the electrode, and a collector of the fourth triode Q4 and a collector of the sixth triode Q6 are both connected to the bioelectric feedback circuit 4. Pulse control terminals of the circuit are the M_0, M_1, M_2 and M_3 pins of the MCU 1 and output high levels at ordinary times, and all the triodes are turned off; when a forward pulse is needed, the M_0 pin and the M_3 pin output low levels, the M_1 pin and the M_2 pin output high levels, the fifth triode Q5 and the sixth triode Q6 are turned on, the fourth triode Q4 and the seventh triode Q7 are turned off, and a current obtained after boosting is input to the electrode by means of the fifth triode Q5, then enters the human body to generate the forward pulse on the human body, and finally is fed back to the bioelectric feedback circuit from the sixth triode Q6; when a reverse pulse is needed, the M_1 pin and the M_2 pin output low levels, the M_0 pin and the M_3 pin output high levels, the fourth triode Q4 and the seventh triode Q7 are turned on, the fifth triode Q5 and the sixth triode Q6 are turned off, the current is input to the electrode by means of the fourth triode Q4 and then enters the human body, and the seventh triode Q7 transmits a signal to the bioelectric feedback circuit to generate the reverse pulse on the human body. In this way, effective control of the pulse is realized.

Figure 5:
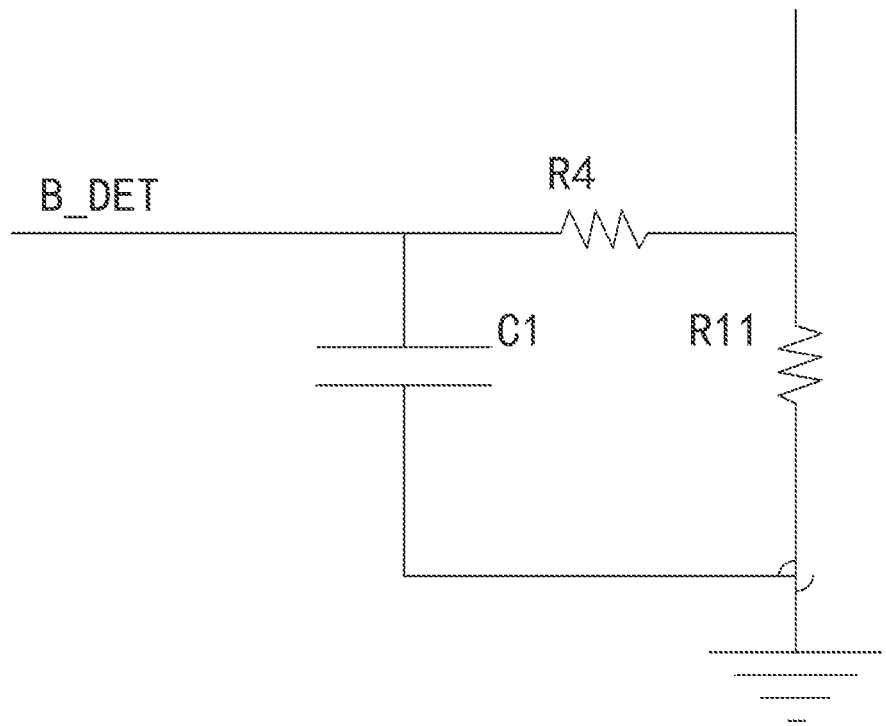
FIG. 5 is a structural diagram of a bioelectric feedback circuit according to one embodiment of the invention.

Further, the bioelectric feedback circuit 4 in this embodiment may adopt a circuit structure shown in FIG. 5. That is, the bioelectric feedback circuit 4 comprises an eleventh resistor R11 and a fourth resistor R4, wherein one terminal of the eleventh resistor R11 is grounded, the other terminal of the eleventh resistor R11 is connected to the fourth resistor R4 and the pulse output control circuit 3, and the other terminal of the fourth resistor R4 is grounded by means of a first capacitor C1 and is connected to the B_DET pin of the MCU 1. The circuit is mainly used for feeding bioelectricity, fed back by the human body, back to the MCU 1. That is, during specific work, a signal input by the pulse output control circuit 3 passes through the eleventh resistor R11 to generate a voltage difference, and then passes through the fourth resistor R4, and an active stable voltage is formed after RC filtering of the first capacitor C1 and is supplied to the MCU 1 for AD detection.

Figure 6:
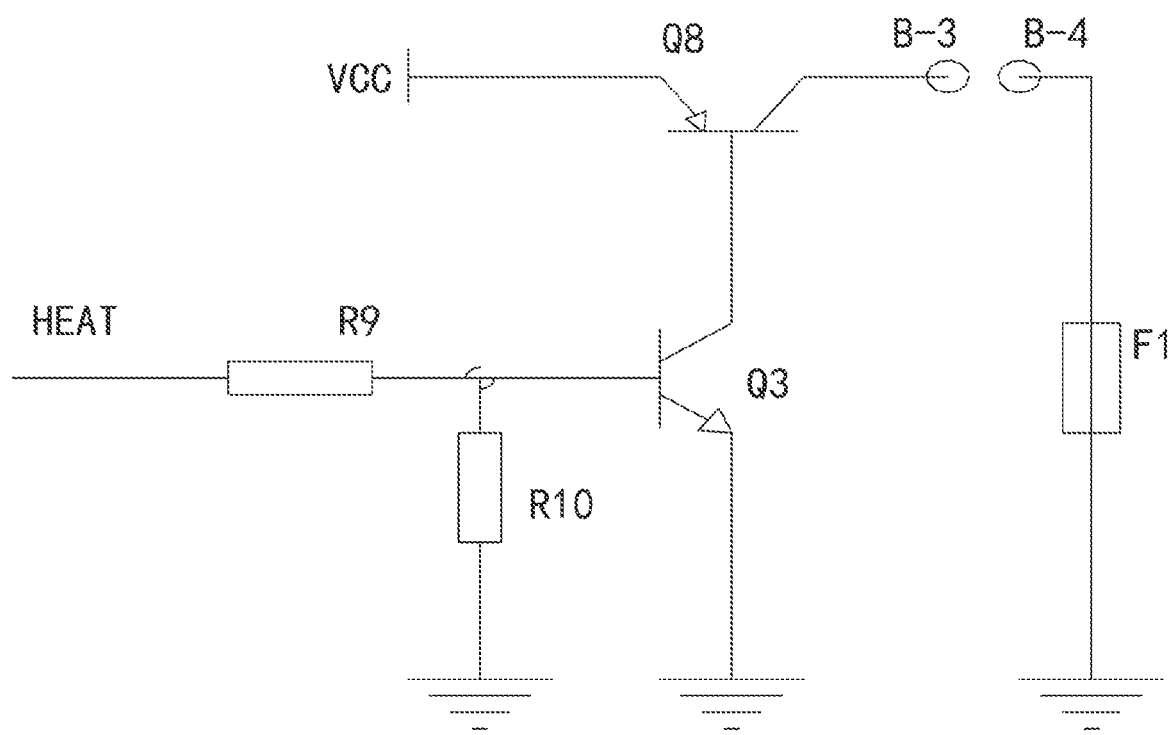
FIG. 6 is a structural diagram of a heating control circuit according to one embodiment of the invention.

Further, the heating control circuit 5 in this embodiment may adopt a circuit structure shown in FIG. 6. That is, the heating control circuit 5 comprises a third triode Q3 and an eighth triode Q8, wherein a base of the third triode Q3 is grounded by means of a tenth resistor R10 and is connected to the HEAT pin of the MCU 1 by means of a ninth resistor R9, a collector of the third triode Q3 is connected to a base of the eighth triode Q8, a power source is accessed to an emitter of the eighth triode Q8, a collector of the eighth triode Q8 is connected to the heating element, and the other end of the heating element is grounded by means of a resettable fuse F1. Temperature control ports B3 and B4 in the circuit are connected to the heating element; the HEAT pin of the MCU 1 outputs a low level at ordinary times, the third triode Q3 is turned off, and the tenth resistor R10 is used to prevent a potential at an IO port from becoming unstable when the MCU 1 is powered on, so that it is ensured that the third triode Q3 is turned off. After the third triode Q3 is turned off, the base of the eighth triode Q8 is at a high level, so the eighth triode Q8 is also turned off, the VCC power source is cut off, and the heating element stops working. When heating is needed, the HEAT pin of the MCU 1 outputs a high level, the third triode Q3 is turned on, the eighth triode Q8 is driven to be turned on, the VCC voltage is loaded to the two ends of the heating element by means of the eighth triode Q8, and the heating element works normally. The MCU 1 is used to control the HEAT pin to output a high or low level to effectively control the working time of the heating element, so that the heating temperature is controlled. Meanwhile, to avoid a large current caused by a short circuit of the heating element, the resettable fuse F1 is added; and the resettable fuse F1 has a low resistance at ordinary times, and when the working current is too large, the resistance of the resettable fuse F1 increases drastically to limit the working current to fulfill a protection function.

The above embodiments are merely preferred ones of the invention, and are not intended to limit the patent scope of the invention. All equivalent structural or flow transformations made based on the contents in the specification and accompanying drawings of the invention, or direct or indirect applications to other related technical fields should also fall within the protection scope of the patent of invention.

What is claimed is:

1. A physiotherapy instrument with an intelligent heating control function based on bioelectric feedback, comprising an Microcontroller Unit (MCU), a boost control circuit, a pulse output control circuit, a bioelectric feedback circuit and a heating control circuit, wherein the MCU is connected to the boost control circuit, the pulse output control circuit, the bioelectric feedback circuit and the heating control circuit, the pulse output control circuit is configured to input electric pulses within a predetermined range to a human body by an electrode, the bioelectric feedback circuit is configured to feed a resistance of the human body back to the MCU, and the MCU is configured to control a heating time of a heating element by the heating control circuit according to the resistance fed back by the bioelectric feedback circuit, so as to control a temperature to rise or fall.

2. The physiotherapy instrument with an intelligent heating control function based on bioelectric feedback according to claim 1, wherein the boost control circuit comprises an inductor, a first triode and a second triode, a base of the first triode is connected to a PUMP pin of the MCU by a first resistor, the inductor has a terminal to which a power source is accessed, as well as a terminal connected to a collector of the first triode, the collector of the first triode is connected with a diode and is connected to a positive pole of the diode, a negative pole of the diode is connected to the pulse output control circuit, is grounded by a charging capacitor and is connected to a collector of the second triode by a third resistor, and a base of the second triode is connected to a DIS_P pin of the MCU by a second resistor.

3. The physiotherapy instrument with an intelligent heating control function based on bioelectric feedback according to claim 1, wherein the pulse output control circuit comprises a fourth triode, a fifth triode, a sixth triode and a seventh triode, a base of the fourth triode, a base of the fifth triode, a base of the sixth triode and a base of the seventh triode are connected to an M_2 pin, an M_0 pin, an M_3 pin and an M_1 pin of the MCU by a sixth resistor, a fifth resistor, an eighth resistor and a seventh resistor respectively, an emitter of the fifth triode and an emitter of the seventh triode are connected to an output terminal of the boost control circuit, a collector of the fifth triode and an emitter of the fourth triode are connected and are both connected to the electrode, a collector of the seventh triode and an emitter of the sixth triode are connected and are both connected to another terminal of the electrode, and a collector of the fourth triode and a collector of the sixth triode are both connected to the bioelectric feedback circuit.

4. The physiotherapy instrument with an intelligent heating control function based on bioelectric feedback according to claim 1, wherein the bioelectric feedback circuit comprises an eleventh resistor and a fourth resistor, the eleventh resistor has a terminal grounded and a terminal connected to the fourth resistor and the pulse output control circuit, and another terminal of the fourth resistor is grounded by a first capacitor and is connected to a B_DET pin of the MCU.

5. The physiotherapy instrument with an intelligent heating control function based on bioelectric feedback according to claim 1, wherein the heating control circuit comprises a third triode and an eighth triode, a base of the third triode is grounded by a tenth resistor and is connected to a HEAT pin of the MCU by a ninth resistor, a collector of the third triode is connected to a base of the eighth triode, a power source is accessed to an emitter of the eighth triode, a collector of the eight triode is connected to the heating element, and another end of the heating element is grounded by a resettable fuse.

\* \* \* \* \*